United States Patent [19]
Watson et al.

[11] Patent Number: 5,855,889
[45] Date of Patent: Jan. 5, 1999

[54] MAMMAGLOBIN, A MAMMARY-SPECIFIC BREAST CANCER PROTEIN

[75] Inventors: Mark A. Watson; Timothy P. Fleming, both of St. Louis, Mo.

[73] Assignee: Washington University, St. Louis, Mo.

[21] Appl. No.: 722,304

[22] Filed: Sep. 30, 1996

Related U.S. Application Data

[62] Division of Ser. No. 455,896, May 31, 1995, Pat. No. 5,668,267.

[51] Int. Cl.$^6$ .............................. G01N 33/53; C07K 7/06; C07K 14/435
[52] U.S. Cl. .................................... 424/185.1; 424/184.1; 530/350; 530/330
[58] Field of Search .............................. 424/184.1, 185.1; 530/350, 330

[56] References Cited

U.S. PATENT DOCUMENTS 5,668,267  9/1997  Watson et al. ......................... 536/23.5

OTHER PUBLICATIONS

Daniel et al. Mapping of linear antigenic sites on the S glycoprotein of a neurotropic murine coronavirus with synthetic peptides: a combination of nine predictive algorithms fails to identify relevant epitopes and peptide immunogenicity is drastically i, 1994.

Hopp et al. Prediction of protein antigenic determinants from amino acid sequences. Proceedings of the National Academy of Scinces, USA. vol. 78, No. 6, pp. 3824–3828, Jun. 1981.

Peeters et al. Structural studies on rat prostatic binding protein. European Journal of Biochemistry. vol. 115, pp. 115–121, 1981.

Watson et al. Isolation of differentially expressed sequence tags from human breast cancer. Cancer Research. vol. 54, pp. 4598–4602, Sep. 1, 1994.

Primary Examiner—Elizabeth C. Kemmerer
Assistant Examiner—Brian Lathrop
Attorney, Agent, or Firm—Howell & Haferkamp, L.C.

[57] ABSTRACT

A purified and isolated DNA sequence and the encoded mammary-specific protein, mammaglobin, are disclosed. Also disclosed are methods for the detecting breast cancer based upon the overexpression and secretion of mammaglobin by breast cancer cells. The methods detect and/or quantitate the presence of mammaglobin or the mRNA encoding mammaglobin.

7 Claims, 7 Drawing Sheets

```
hCC10  -31  MKLAVTLTLVTLALCCSSASAEICPSFQRVFETLLMDTPSS-
                 | | |   |  | |   | |       |      |   |
hMaM    01  MKLLMVLMLAALSQHCY-A-GSGCPLLENVISKTINPQVSKT
               |   | || |    ||   || || | |  |   ||| |||
rPSC3   01  MKLVFLPLLVTIPICCY-ASGSGCSILDEVRGTINSTVTLH hCC10   20  -VEAAMELFSPDQDMREAGAQLKKLVDTLPQK--PRESIIKL
                     ||   | |    ||   |      |||
hMaM    41  EEKELLQEFIDDNATTNAIDELKECF--LNQTDETLSNVEVF
              ||  ||   | |  |     | ||    ||  |||  ||  |
rPSC3   42  DMMKLVKPYVQDHFTEKAVKQFKQCF--LDQIDKTLENVGVM hCC10   61  MEKLAQSSIKN
            | | |  |  |
hMaM    82  QQLIYDSSILDLF
            |     |   |
rPSC3   83  MEAIFNSESIQQPS
```

Figure 1

```
                    9            18           27           36           45           54
5' GAC AGC GGC TTC CTT GAT CCT TGC CAC CCG CGA CTG AAC ACC GAC AGC AGC AGC 63           72           81           90           99          108
CTC ACC ATG AAG TTG CTG ATG GTC CTC ATG CTG GCG GCC CTC TCC CAG CAC TGC
        Met Lys Leu Leu Met Val Leu Met Leu Ala Ala Leu Ser Gln His Cys
         1                                      10

117          126          135          144          153          162
TAC GCA GGC TCT GGC TGC CCC TTA TTG GAG AAT GTG ATT TCC AAG ACA ATC AAT
Tyr Ala Gly Ser Gly Cys Pro Leu Leu Glu Asn Val Ile Ser Lys Thr Ile Asn
             20                                      30

171          180          189          198          207          216
CCA CAA GTG TCT AAG ACT GAA TAC AAA GAA CTT CTT CAA GAG TTC ATA GAC GAC
Pro Gln Val Ser Lys Thr Glu Tyr Lys Glu Leu Leu Gln Glu Phe Ile Asp Asp
                     40                                           50

225          234          243          252          261          270
AAT GCC ACT ACA AAT GCC ATA GAT GAA TTG AAG GAA TGT TTT CTT AAC CAA ACG
Asn Ala Thr Thr Asn Ala Ile Asp Glu Leu Lys Glu Cys Phe Leu Asn Gln Thr
                             60                                          70

279          288          297          306          315          324
GAT GAA ACT CTG AGC AAT GTT GAG GTG TTT ATG CAA TTA ATA TAT GAC AGC AGT
Asp Glu Thr Leu Ser Asn Val Glu Val Phe Met Gln Leu Ile Tyr Asp Ser Ser
                                     80

333          342          351          360          369          378
CTT TGT GAT TTA TTT TAA CTT TCT GCA AGA CCT TTG GCT CAC AGA ACT GCA GGG
Leu Cys Asp Leu Phe ***
 90

387          396          405          414          423          432
TAT GGT GAG AAA CCA ACT ACG GAT TGC TGC AAA CCA CAC CTT CTC TTT CTT ATG 441          450          459          468          477          486
TCT TTT TAC TAC AAA CTA CAA GAC AAT TGT TGA AAC CTG CTA TAC ATG TTT ATT

495
TTA ATA AAT TGA TGG CA 3'
```

Figure 2

```
hCC10  -21  MKLAVTLTLVTLALGSSASAEICPSFQRVIETLLMDTPSS-
                   |    |     | ||  |  | |  |     ||
hMaM    01  MKLLMVLMLAALSQHCY-A-GSGCPLLENVISKTINPQVSKT
                |   |    |    | ||| |||  |    |||| |||
rPSC3   01  MKLVFLFLLVTIPICCY-ASGSGCSILDEVIRGTINSTVTLH hCC10   20  -MEAAMELFSPDQDMREAGAQLKKLVDTLPQK--PRESIIKL
               |    |       |     |     |         ||
hMaM    41  EIKELLQEFIDDNATTNAIDELKECF--INQTDETLSNVEVF
             |   ||  ||      | ||   ||   || ||| || |
rPSC3   42  DLMKLVKPYVQDHFTEKAVKQFKQCF--LDQFDKTLENVGVM hCC10   61  MEKIAQSILN
                |  ||
hMaM    82  MQLIYDISLDLF
              |   ||
rPSC3   83  MEAIFNIESIQQPS
```

MAMMAGLOBIN, A MAMMARY-SPECIFIC BREAST CANCER PROTEIN

This is a divisional of application Ser. No. 08/455,896 filed on May 31, 1995, now U.S. Pat. No. 5,668,267.

BACKGROUND OF THE INVENTION (1) Field of the Invention

This invention relates generally to the field of breast cancer pathogenesis and, more particularly, to a cDNA sequence and encoded mammary-specific protein for use in detecting and treating breast cancer.

(2) Description of the Related Art

Breast cancer is one of the most common and potentially lethal of cancers. Although early diagnosis and treatment can reduce morbidity and mortality related to the disease, the positive predictive value of mammography has been estimated to be only about 25% (Hall et al., *N Engl J Med* 327: 319–328, 1992 which is incorporated by reference). It would, therefore, be desirable to have a means for detecting the cancer earlier than the cancer can be detected using mammography and a genetic or biochemical marker might be able to provide such means to complement and increase the predictive value of mammography. (Hayes, *Hematol Oncol Clin N Am* 8: 485, 1994 which is incorporated by reference).

The development of breast cancer is accompanied by a number of genetic changes (For review see Porter-Jordan, *Hematol Oncol Clin N Am* 8: 73, 1994 which is incorporated by reference). Such changes include gross chromosomal alterations and loss of genetic markers (Devilee et al, *Biochim Biophys Acta* 1198: 113, 1994; Callahan et al, *J Cell Biochem Suppl* 17: 167, 1993 which are incorporated by reference). The progression of breast neoplasia has also been shown to result in qualitative and quantitative changes in expression of previously identified genes that encode growth factors and their receptors (Zajchowski et al., *Cancer Res* 48: 7041, 1988 which is incorporated by reference), structural proteins (Trask et al., *Proc Natl Acad Sci* 87: 2319, 1990 which is incorporated by reference), second messenger proteins (Ohuchi et al., *Cancer Res* 26: 2511, 1986 which is incorporated by reference), and transcription factors (Harris, *Adv Cancer Res* 59: 69: 1992 which is incorporated by reference). These changes in gene expression could potentially form the basis for developing a breast cancer marker, although the precise role of these gene changes in the pathogenesis of breast carcinoma in patient biopsy samples is not well understood.

In addition to providing a genetic or biochemical marker for breast cancer for early detection of the disease, it would also be desirable to have a tumor marker that might provide an estimation of prognosis, a means for selection and evaluation of therapy and a means for the targeting of therapy. Although a number of tissue markers have been identified, none are sufficiently sensitive or tumor specific to be ideally suited for diagnosis or for screening the general population. (Id.). Thus, there remains a continuing need for a breast cancer marker such as a gene along with its expressed protein that can be used to specifically and selectively identify the appearance and pathogenic development of breast cancer in a patient.

Using a modified differential display polymerase chain reaction technique to isolate differentially expressed sequence tags from mammary carcinoma, several sequence fragments were isolated that were uniquely expressed in neoplastic mammary epithelial tissue as compared to normal tissue controls (Watson and Fleming, *Cancer Res* 54: 4598–4602, 1994 which is incorporated by reference). The discovery of one of these sequence tags identified as DEST002 has led to the discovery and isolation of the novel full length cDNA and encoded protein now referenced as mammaglobin. The cDNA and protein are both new.

SUMMARY OF THE INVENTION

Briefly, therefore, the present invention is directed to the identification of novel genes whose expression is increased in breast cancer and to the isolating of cDNA's from the mRNA's of these genes. Accordingly, applicants have succeeded in discovering a novel cDNA and the encoded mammary-specific secretory protein, mammaglobin. The cDNA is in purified and isolated form and identified as SEQ ID NO: 1 and the encoded protein, mammaglobin is in purified and isolated form and identified as SEQ ID NO: 2.

Mammaglobin is overexpressed in 27% of stage I primary breast cancer tumors. This suggests that dysregulation of the mammaglobin gene occurs early and frequently in breast cancer. The discovery of mammaglobin and its cDNA, therefore, provide the basis for the development of novel methods and compositions for the detection and treatment of breast neoplastic disease in humans and other mammals.

Thus, the present invention is also directed to novel methods for detecting the presence of breast neoplasia cells in a sample. In one embodiment cDNA encoding mammaglobin or a derivative of said cDNA is used to detect the presence of mammaglobin mRNA in a sample. The method comprises the steps of: (a) providing a polynucleotide containing a nucleotide sequence having the sequence of SEQ ID NO: 1 or a derivative thereof, (b) incubating the nucleotide sequence with the sample under conditions in which the sequence can hybridize with mRNA from breast neoplasia cells, and (c) detecting the existence of a DNA-RNA hybridization complex.

Another aspect the present invention provides for a kit for detecting the presence of breast neoplasia cells in a sample. The kit comprises a polynucleotide containing a nucleotide sequence having the sequence of SEQ ID NO: 1 or a derivative thereof packaged in a container.

In another embodiment of the present invention, mammaglobin or a derivative thereof is used to detect the presence of cDNA that is reverse transcribed from mammaglobin mRNA in a sample. The method comprises the steps of: (a) producing a cDNA from mRNA using the reverse transcription method in a sample obtained from a patient, (b) providing two oligomers which are primers for the polymerase chain reaction method and which flank or lie within a cDNA encoding mammaglobin, and (c) amplifying the cDNA encoding mammaglobin by the polymerase chain reaction method. The two oligomers comprise SEQ ID NO: 3 and SEQ ID NO: 4.

Another embodiment to the present invention provides a kit for detection of the presence of breast neoplasia cells in a sample. The kit comprises two oligomers which are primers for the polymerase chain reaction method and which are flank or lie within a cDNA encoding mammaglobin packaged in a container. The two oligomers comprise SEQ ID NO: 3 and SEQ ID NO: 4.

In another embodiment of the present invention, the presence of the mammaglobin expressed by a tumor cell is detected in a sample using specific antibodies to the protein, mammaglobin. The specific antibodies can be polyclonal or monoclonal antibodies.

Among the several advantages found to be achieved by the present invention, therefore, may be noted the provision of a nucleotide sequence and encoded amino acid sequence that can serve as markers for breast cancer cells; the provision of methods for early detection of the presence of breast neoplasia cells; the provision of means for detecting breast cancer that can complement mammography and increase the predictive value; and the provision of methods that can provide an estimation of prognosis; and the provision of markers that will allow the targeting of therapy.

BRIEF DESCRIPTION OF THE DRAWINGS

FIG. 4 illustrates (A) the Northern blot analysis of hybridization of the human cDNA sequence encoding the mammary-specific protein, mammaglobin (hMAM), to mRNA expressed by tissues from breast neoplasia, normal breast and other adult tissues and (B) the analysis of RT/PCR amplified samples of tissues from breast neoplasia, normal breast and other adult tissues;

DESCRIPTION OF THE PREFERRED EMBODIMENTS

Figure 2:
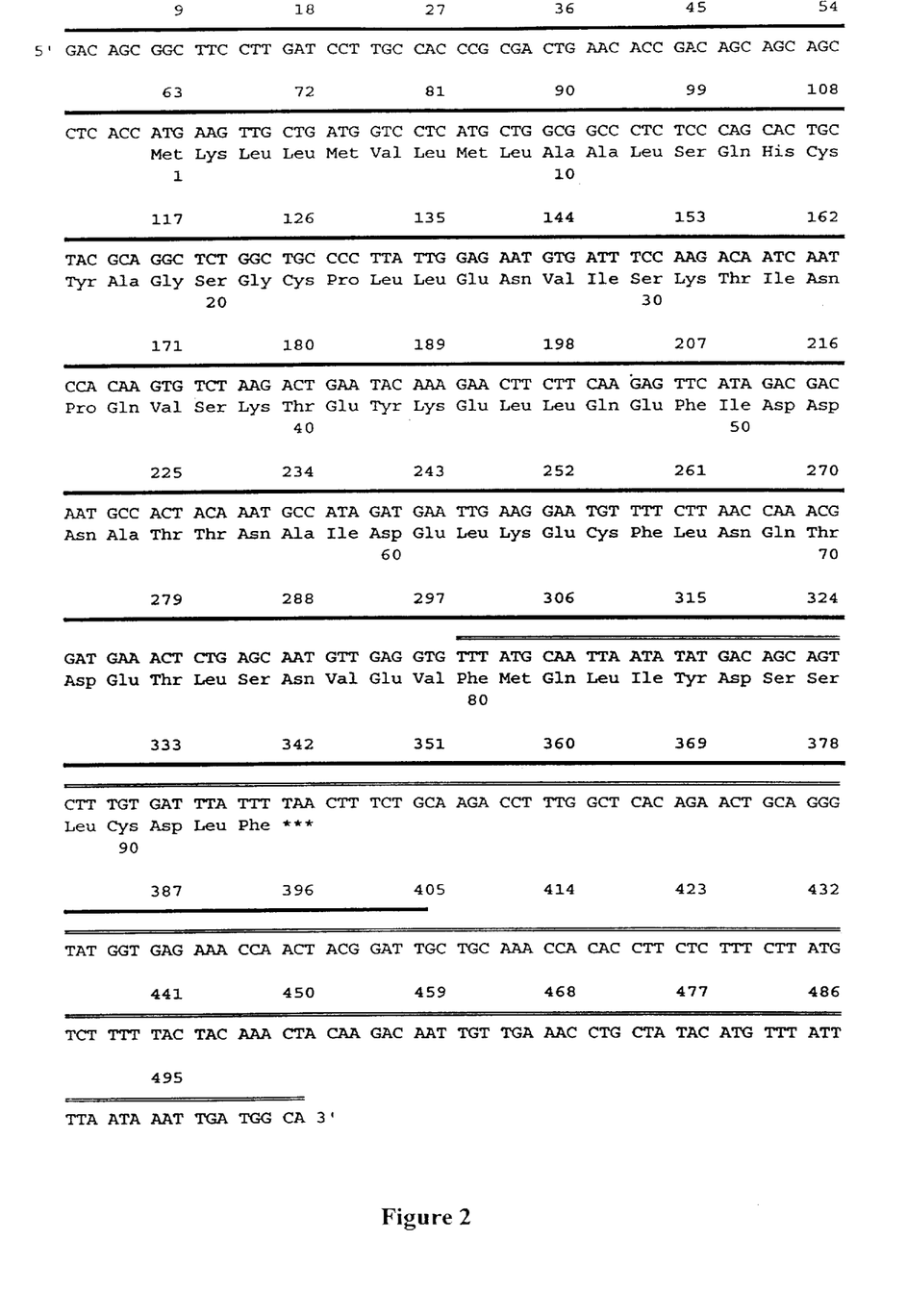
FIG. 2 illustrates the human cDNA sequence of SEQ ID NO: 1 (nucleotides numbered above) and the amino acid sequence of the encoded the mammary-specific protein, mammaglobin (SEQ ID NO: 2)(amino acids numbered below), the solid bar illustrating the 403 bp fragment (SEQ ID NO: 5) isolated by the RACE PCR method and the open bar indicating the 206 bp DEST002 sequence (SEQ ID NO: 6)

One aspect of the present invention is based upon the identification and sequencing of the cDNA identified as SEQ ID NO: 1 which encodes a mammary-specific secretory protein, mammaglobin, identified by SEQ ID NO: 2 (FIG. 2). As described below, the full length mammaglobin cDNA was isolated starting from tumor cell mRNA that was reverse transcribed, amplified using the technique of PCR and subcloned into expression vectors. In addition, the protein, mammaglobin, encoded by the cDNA was identified and characterized.

Figure 1:
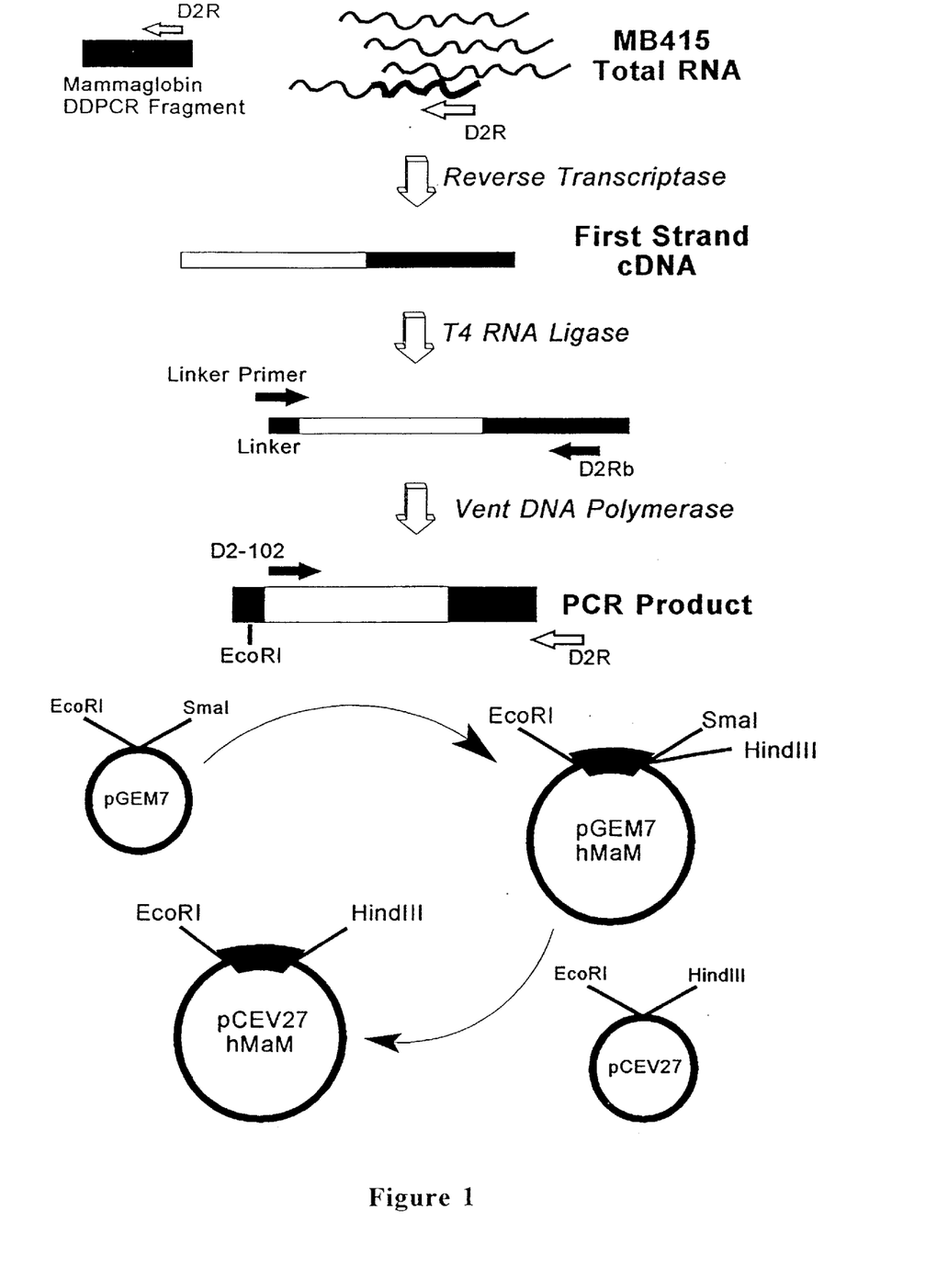
FIG. 1 illustrates the strategy used to isolate the full length mammaglobin cDNA using the Rapid amplification of cDNA Ends (RACE) Polymerase Chain Reaction (PCR) technique and subsequent subcloning into vectors pGEM7Z and pCEV27.

Using the anonymous sequence tag previously designated DEST002, it was demonstrated that the corresponding gene product, which was up until now unknown but herein identified as mammaglobin, is particularly abundant in the breast cancer tumor cell line MDA-MB415. To isolate the full length mammaglobin cDNA, the mRNA was reverse transcribed from this cell line and cloned using the RACE PCR technique (Edwards et al. *Nucleic Acids Research* 19: 5227–32, 1991 which is incorporated by reference). This technique is based upon the strategy of ligation of single-stranded oligodeoxyribonucleotide to the 3' end of single-stranded cDNA. The method by which the mammaglobin cDNA was isolated is represented schematically in FIG. 1. The full length 503 bp cDNA sequence (SEQ ID NO: 1) was deduced from the sequence information obtained from the 403 bp fragment (SEQ ID NO: 5) (FIG. 2) isolated by this technique along with sequence information previously obtained from the corresponding DEST sequence (DEST002, SEQ ID NO: 6) in our earlier study (Watson and Fleming, supra) (FIG. 2). The full length mammaglobin cDNA and the encoded polypeptide is shown in FIG. 2. Within the 503 bp cDNA is a 279 bp open reading frame which encodes a polypeptide of 93 amino acids and predicted molecular mass of 10.5 kD (FIG. 2). The first 19 residues of this open reading frame also predict a hydrophobic peptide signal sequence. The initial methionine of the open reading frame contains a near-perfect Kozak consensus sequence (Kozak, *Cell* 22: 7–8, 1980 which is incorporated by reference). The 60 bp upstream of this sequence contain no other in-frame methionines or translational stops. The 3' untranslated sequence of the cDNA constitutes 163 bp and contains a polyadenylation signal, AATAAA, 12 bp upstream of the priming site of the original DEST002 sequence. These data indicate that the full length mammaglobin cDNA has been isolated.

A search for DNA sequences similar to the mammaglobin cDNA sequence in Genbank using the BLAST algorithm (Benson et al., *Nucl Acid Res* 21: 2963–2965, 1993; Altschul et al, *J Mol Biol* 215: 403–410, 1990 which are incorporated by reference), identified no obvious DNA sequence homologies. Thus, mammaglobin cDNA is believed to be a novel, heretofore unknown DNA sequence.

Figure 3:
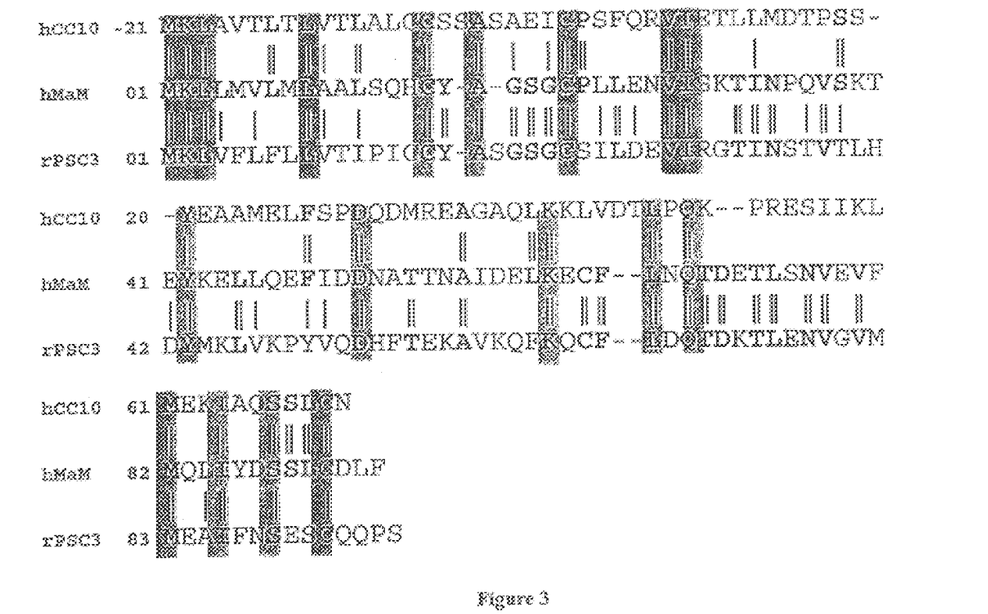
FIG. 3 illustrates the amino acid sequence of the mammary-specific protein, mammaglobin (hMAM), (SEQ ID NO: 2) compared to rat prostatic steroid binding protein subunit C3 (rPSC3)(SEQ ID NO: 7) and human clara cell 10 kD protein (hCC10)(SEQ ID NO: 8) with identities marked by bold letters and double lines and structurally similar amino acids marked by single lines.

A search of other polypeptides for sequences related to mammaglobin revealed an amino-acid sequence homology between mammaglobin and other polypeptides. Mammaglobin exhibited 42% amino acid identity (58% including conservative substitutions) with rat prostatic steroid binding protein (prostatein) subunit C3 (rPSC3) (FIG. 3) (SEQ ID NO: 7). Rat prostatic steroid binding protein is a major secretory protein in the rat ventral prostate consisting of a tetrameric protein composed of two different dimeric subunits; C3/C1 and C3/C2 (Parker et al., *Ann N Y Acad Sci* 438: 115–124; Parker et al., *J Steroid Biochem* 20: 67–71, 1984 which are incorporated by reference). The C1, C2, and C3 genes all encode approximately 6 kD secretory proteins and are thought to have arisen from gene duplication, but while the C1 and C2 genes show strong homology to each other, they are much less similar to the C3 gene. Correspondingly, mammaglobin shows no sequence homology with the C1 or C2 proteins.

As noted above, prostatic steroid binding protein (prostatein) is the major secretory protein in the rat ventral prostate and its expression is regulated by androgenic steroids (Parker et al, *Ann N Y Acad Sci* 438: 115–24, 1984; Parker et al, *J Steroid Biochem* 20: 67–71, 1984 which are incorporated by reference). Another protein, human estramustin-binding protein (hEMBP) has been reported to be expressed in human prostate, human breast cancer and human malignant melanoma. (Bjork et al, *Cancer Res* 42: 1935–1942, 1982; Bjork et al, *Anticancer Res* 11: 1173–82, 1991 which are incorporated by reference). Human estramustin-binding protein is immunochemically similar to rat estramustin-binding protein, which has been postulated to be identical to rat steroid-binding protein, prostatein. As noted above, the amino acid sequence of mammaglobin exhibited 42% amino acid identity and 58% homology including conservative substitutions with the C3 subunit of prostatein. Thus it is possible that mammaglobin could be in some way related to hEMBP. However, while both prostatein and hEMBP are detected in the prostate gland, mammaglobin mRNA is completely absent in this tissue. Hence, mammaglobin is neither the same protein nor a subunit of hEMBP and, furthermore, the sequence of hEMBP has not been determined so that it is not known whether there is even any similarity of mammaglobin with some fragment or subunit of hEMBP.

Although recent reports have demonstrated the rPSC3 promoter fused to SV40 T antigen produces both prostatic and mammary carcinomas in transgenic mice (Maroulakou et al., *Proc Nat Acad Sci U.S.* 91:11236–11240, 1994; Sandmoller et al, *Oncogene* 9: 2805–2815, 1994 which are incorporated by reference), the true biological function of this protein is unknown. Furthermore, notwithstanding the hypothesized relationship of rat prostatic steroid binding protein to human EMBP, no human polypeptide or human gene corresponding to rPSC3 has been identified. Thus, mammaglobin and the cDNA encoding mammaglobin represent novel sequences heretofore unknown.

Using manual alignment with other sequences that had less significant BLAST scores with both mammaglobin and rPSC3 protein sequences, we identified other homologies with human clara cell 10 kD protein (hCC10) (SEQ ID NO: 8) (Peri et al, *J Clin Invest* 92:2099–2109, 1993 which is incorporated by reference) (FIG. 3) and, in addition, with rabbit and mouse uteroglobin proteins (Miele et al., *Endocrine Rev* 8: 474–90, 1987; Cato and Beato, *Anticancer Res* 5: 65–72, 1985; Miele et al., *J Endocrinol Invest* 17: 679–692, 1994 which are incorporated by reference). These homologies, depending on species, were 26% identity or 40% including conservative substitutions. In particular, a number of amino acids were perfectly conserved among all proteins, including Cys-3 and Cys-69 which are known to play a role in disulfide bond formation between uteroglobin subunits (see below). These homologies suggest that mammaglobin is a novel member of a small family of proteins that are secreted by epithelial cells (Miele et al, 1994, supra).

The hCC10 gene is the human homologue of rabbit and mouse uteroglobin genes (Peri et al, *J Clin Invest* 92: 2099–2109, 1993 which is incorporated by reference). Uteroglobin was originally characterized as a secretory protein in rabbit uterus, but has since been found in other epithelial organs including lung, breast and prostate. Unlike rat prostatein, uteroglobin is a homodimeric protein coupled by two disulfide linkages at the conserved residues Cys-2 and Cys-69 (Miele et al, 1994, supra). Although uteroglobin gene transcription is regulated by steroid hormones, the ability of the protein itself to bind progesterone or other steroid hormones is controversial and again, the true biological function of this protein is unknown (Miele et al., 1994, supra).

Figure 4A:
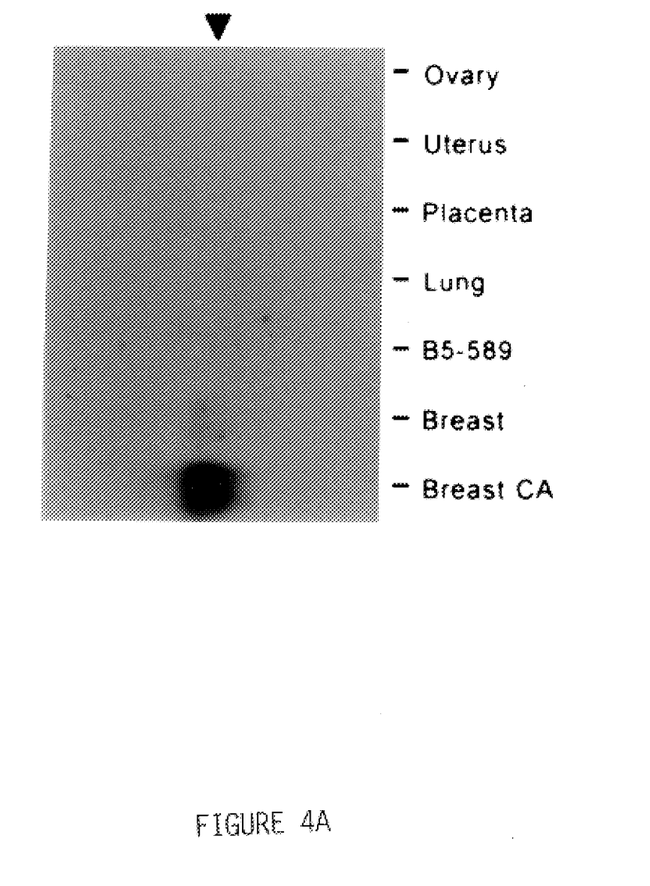

Mammaglobin expression is restricted to the mammary gland. This is in contrast to the observation that rPSC3 is expressed in rat ventral prostate (Parker et al., *Ann N Y Acad Sci* 438: 115–1124, 1984), and the expression of hCC10/uteroglobin in numerous tissues including lung, uterus, prostate, and breast (Miele et al., 1987, supra; Cato and Beato, supra; Miele et al., 1994 supra). Because of the sequence homology between mammaglobin and these proteins, we determined the pattern of tissue specific expression. The 500 bp mammaglobin message was easily detected in tumor specimen 2410 (the tissue from which this original sequence tag was isolated) and to a much less extent in normal human breast tissue (FIG. 4A). The mammaglobin message could not be detected in the immortalized breast epithelial cell line B5-589. Expression of mammaglobin was also undetectable in human uterus and lung, two sites of uteroglobin expression.

Figure 4B:
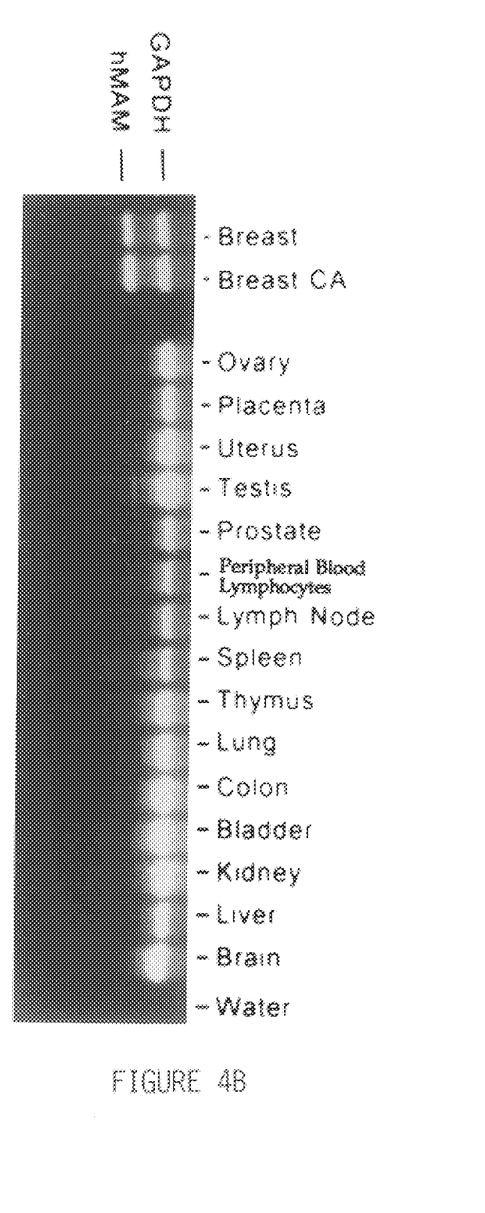

Amplification using RT/PCR detected mammaglobin mRNA in both tumor 2410 and normal breast tissue, but not in 15 other tissues surveyed, including tissues that normally express rPSC3 and uteroglobin (lung, uterus, prostate), hormonally responsive and steroidogenic tissues (ovary, testis, placenta), and other secretory epithelial organs (colon) (FIG. 4B). Therefore, the expression of mammaglobin mRNA is relatively specific for mammary tissue.

Based on the studies in this report, mammaglobin is a relatively mammary-specific protein. Two other genes known to be overexpressed in breast carcinoma are erb-B and cyclin D (Jardines et al, *Pathology* 61: 268–282, 1994; Keyomars and Pardee, *Proc Nat Acad Sci* U.S. 90: 1112–1116, 1993 which is incorporated by reference). Unlike the overexpression of erb-B or cyclin D, the overexpression of mammaglobin may reflect a more specific alteration of the mammary epithelial cell rather than a general increased growth potential or mitotic rate. As such, appearance of mammaglobin gene dysregulation may have more specific import for the therapeutic vulnerability or clinical course of a tumor.

Mammaglobin expression could not be detected in normal lymph nodes or peripheral lymphocytes at the level of sensitivity afforded by a single step RT/PCR assay. This suggests that analysis of mammaglobin transcripts in peripheral lymph nodes may be useful for detecting occult breast cancer metastases, as has been suggested for other epithelial specific genes (Schoenfeld et al., *Cancer Res* 54: 2986–90 which is incorporated by reference).

Figure 5:
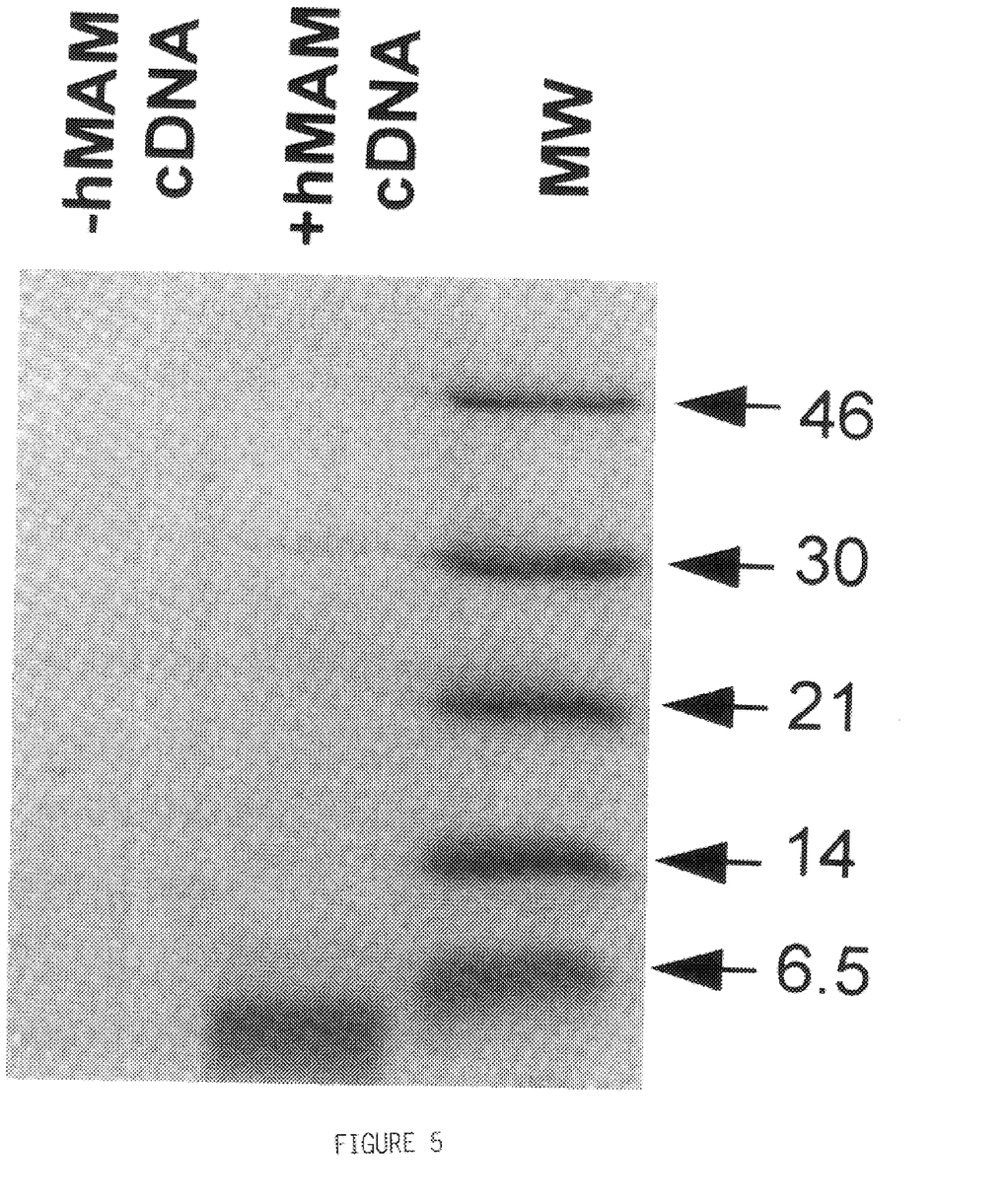
FIG. 5 illustrates the translation of the mammary-specific cDNA sequence in an in vitro rabbit reticulocyte lysate assay system.

To demonstrate that the mammaglobin cDNA encoded a translatable protein, the cDNA clone was used in an In vitro translation assay. FIG. 5 shows the protein product from a rabbit reticulocyte lysate programmed with the mammaglobin cDNA. An approximately 6 kD protein is generated using the mammaglobin cDNA. The apparent molecular weight is smaller than that predicted from conceptual translation of the open reading frame, but this finding is commonly observed with rabbit and human uteroglobin translation products as well.

Figure 6:
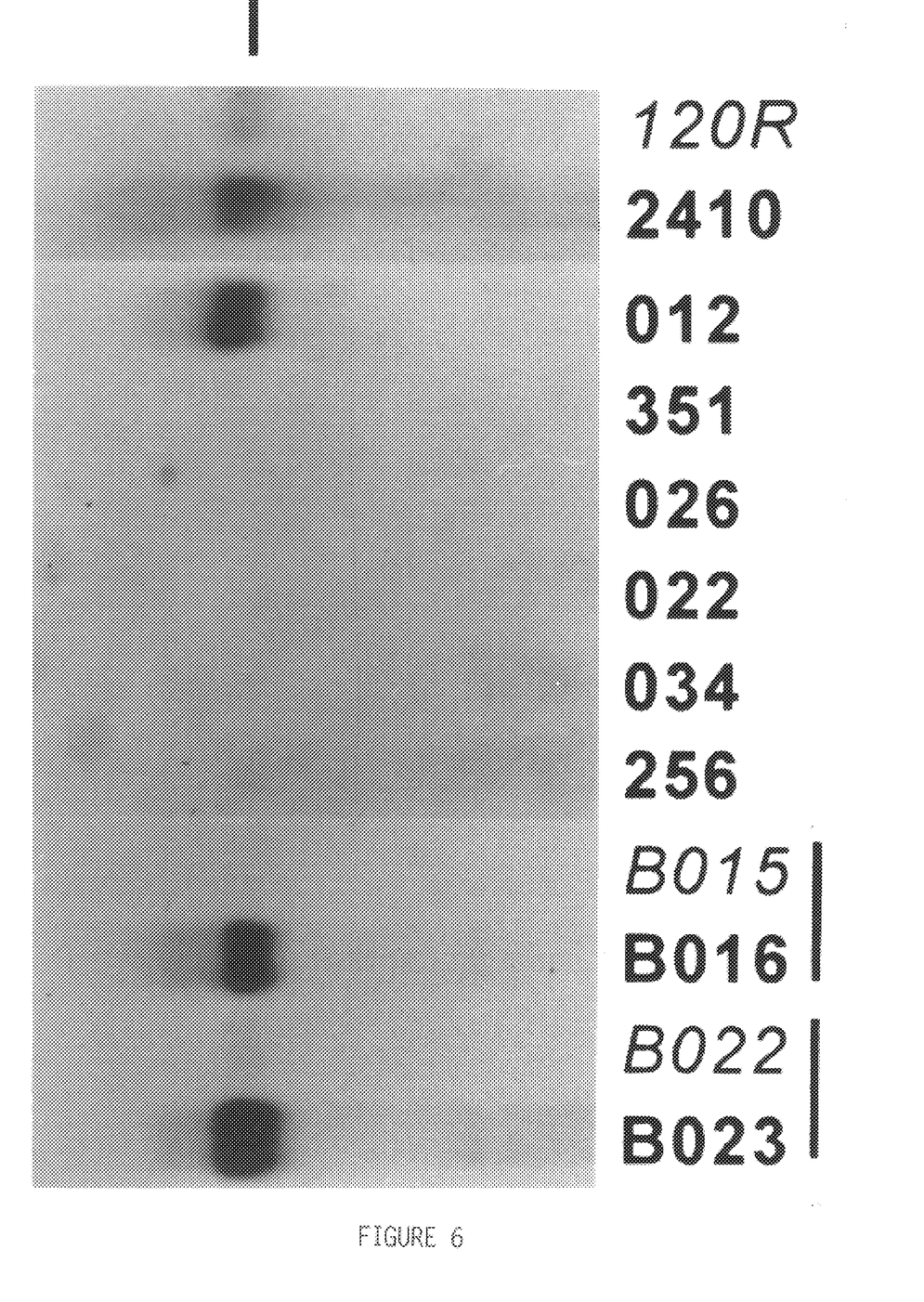
FIG. 6 illustrates Northern blot hybridization with the cDNA encoding mammaglobin detecting mRNA in tumor 2410, in tumors from three of eight other patients (shown in bold), and to a lesser extent, in normal breast tissue (shown in italics) comparing in two cases, mammaglobin expression in tumor tissue and patient matched normal tissue.

Although we detected overexpression of mammaglobin RNA in one tumor specimen (i.e. 2410), it was not clear at what frequency this overexpression is seen in other breast carcinomas. We therefore examined a panel of fifteen, stage I primary breast carcinomas of differing histological types by Northern blot hybridization with the mammaglobin cDNA probe. Because of potential variability in expression due to environment influences (e.g. patient hormonal status), we also sought to compare tumor specimens directly with patient-matched normal breast tissues samples, although this was not possible in many cases. As shown in FIG. 6, the 500 bp mammaglobin mRNA was again detected in normal breast tissue and tumor 2410. Mammaglobin was also detected in three other tumors, two of which demonstrated little or no expression in patient-matched normal tissue. In all, 4 of 15 (27%) of tumors examined overexpressed mammaglobin mRNA. These data suggest that overexpression of mammaglobin is not unique to a single tumor specimen and is, in fact, relatively frequent among primary breast tumors. Furthermore, the fact that all tumors examined were stage I suggests that this dysregulation occurs relatively early in the progression of breast neoplasia.

Because Applicants believe mammaglobin is likely to be a secreted protein, its presence would be expected to be detectable in sera from patients whose tumor overexpresses this gene product. As such, mammaglobin is likely to be as clinically useful as prostate specific antigen (PSA) and other solid tumor markers for managing patients with breast cancer (Tumor markers in diagnostic pathology, *Clin Lab Med* 10: 1–250, 1990 which is incorporated by reference).

We determined the prevalence of mammaglobin as a tumor marker in the general population of breast cancer tumors by examining the expression of mammaglobin in several primary breast carcinomas. Although the number of specimens examined in this study was small, 27% of tumors evaluated overexpressed mammaglobin mRNA. This percentage is comparable to the prevalence of other genetic alterations such as erb-B amplification and p53 mutation (Slamon et al. *Sci* 244: 707–712, 1989; Thor et al, *J Nat'l Cancer Inst* 84: 845–855, 1992 which are incorporated by reference). Furthermore, because we have restricted our analysis to stage I tumors, overexpression of mammaglobin would actually be more prevalent than any other genetic alteration reported in this subgroup of tumors (Alllerd et al, *J Nat'l Cancer Inst* 85: 200–206, 1993 which is incorporated by reference).

The identification of mammaglobin as a breast cancer marker provides the basis for another aspect of the present invention, which involves methods for detecting the presence of breast cancer in a patient. The term "detection" as used herein in the context of detection of breast neoplastic disease is intended to be a comprising aspect of the determining of the presence of breast cancer in a patient, the distinguishing of breast cancer from other diseases, the estimation of prognosis in terms of probable outcome of the disease and prospect for recovery, the monitoring of the disease status or the recurrence of the disease, the determining of a preferred therapeutic regimen for the patient and the targeting of antitumor therapy.

The method for detecting breast cancer comprises hybridizing a polynucleotide to mRNA from breast neoplasia cells. The polynucleotide comprises SEQ ID NO: 1 or a derivative of SEQ ID NO: 1. By derived from a nucleotide sequence it is meant that the derived nucleotide sequence is substantially the same as the sequence from which it is derived in that the derived nucleotide sequence has sufficient sequence complementarity to the sequence from which it is derived to hybridize to mRNA from breast neoplasia cells under the same stringency conditions that the sequence from which it is derived hybridizes to the mRNA from breast neoplasia cells.

The derived nucleotide sequence is not necessarily physically derived from the nucleotide sequence, but may be generated in any manner including for example, chemical synthesis or DNA replication or reverse transcription or transcription.

To detect the presence of mRNA encoding mammaglobin in a detection system for breast cancer, a sample is obtained from a patient. The sample can be a tissue biopsy sample or a sample of blood, plasma, serum or the like. The sample may be treated to extract the nucleic acids contained therein. The resulting nucleic acid from the sample is subjected to gel electrophoresis or other size separation techniques.

Detection involves contacting the nucleic acids and in particular the mRNA of the sample with a DNA sequence serving as a probe to form hybrid duplexes. The term "probe" refers to a structure comprised of a polynucleotide which forms a hybrid structure with a target sequence, due to complementarity of probe sequence with a sequence in the target region.

Detection of the resulting duplex is usually accomplished by the use of labeled probes. Alternatively, the probe may be unlabeled, but may be detectable by specific binding with a ligand which is labeled, either directly or indirectly. Suitable labels and methods for labeling probes and ligands are known in the art, and include, for example, radioactive labels which may be incorporated by known methods (e.g., nick translation or kinasing), biotin, fluorescent groups, chemiluminescent groups (e.g., dioxetanes, particularly triggered dioxetanes), enzymes, antibodies, and the like.

When using the cDNA encoding mammaloglobin or a derivative thereof as a probe, high stringency conditions can be used in order to prevent false positives. When using sequences derived from mammaglobin, less stringent conditions can be used. The stringency of hybridization is determined by a number of factors during hybridization and during the washing procedure, including temperature, ionic strength, length of time and concentration of formamide. These factors are outlined in, for example, Sambrook et al. (*Molecular Cloning: A Laboratory Manual,* 2d ed., 1989).

In order to increase the sensitivity of the detection in a sample of mRNA encoding mammaglobin, the technique of reverse transcription/polymerization chain reaction (RT/PCR) can be used to amplify cDNA transcribed from mRNA encoding mammaglobin. The method of RT/PCR is well known in the art (for example, see Watson and Fleming, supra).

The RT/PCR method can be performed as follows. Total cellular RNA is isolated by, for example, the standard guanidium isothiocyanate method and the total RNA is reverse transcribed. The reverse transcription method involves synthesis of DNA on a template of RNA using a reverse transcriptase enzyme and a 3' end primer. Typically, the primer contains an oligo(dT) sequence. The cDNA thus produced is then amplified using the PCR method and mammaglobin specific primers. (Belyavsky et al, *Nucl Acid Res* 17: 2919–2932, 1989; Krug and Berger, *Methods in Enzymology,* Academic Press, N.Y., Vol.152, pp. 316–325, 1987 which are incorporated by reference)

The polymerase chain reaction method is performed using two oligonucleotide primers that are complementary to the two flanking regions of the DNA segment to be amplified. The upstream and down stream primers are typically from 20 to 30 base pairs in length and hybridize to the flanking regions for replication of the nucleotide sequence. The polymerization is catalyzed by a DNA-polymerase in the presence of deoxynucleotide triphosphates or nucleotide analogs to produce double-stranded DNA molecules. The double strands are then separated by any denaturing method including physical, chemical or enzymatic. Commonly, the method of physical denaturation is used involving heating the nucleic acid, typically to temperatures from about 80° C. to 105° C. for times ranging from about 1 to 10 minutes. The process is repeated for the desired number of cycles.

The primers are selected to be substantially complementary to the strand of cDNA being amplified. Therefore, the primers need not reflect the exact sequence of the template, but must be sufficiently complementary to selectively hybridize with the strand being amplified.

Following amplification, the PCR product is then detected by ethidium bromide staining (Sambrook, et al., 1989, supra).

In another embodiment of the present invention, the mammaglobin cDNA sequence or derivative thereof can be used to characterize any alteration of the mammaglobin gene (i.e. gene rearrangement, gene amplification, or gene deletion) in a specimen from a breast-cancer patient. This provides a method whereby patient specimens or samples, which do not contain intact mRNA, can still be examined for changes in gene structure.

In one application of this technique, the mammaglobin cDNA sequence or derivative thereof is hybridized to patient genomic DNA that had been isolated from a patient's tumor, normal tissue, or lymphocytes and digested with one or more restriction endonucleases. Using the Southern blot protocol, which is well known in the art, this assay determines whether a patient or a patient's breast tumor has a mammaglobin-gene, which was deleted, rearranged, or amplified. Detection of these changes can then provide important information useful for predicting prognosis and for patient management.

In a second application of this technique, one or more pairs of oligonucleotide primers based on the mammaglobin cDNA sequence or derivative thereof could be used in the polymerase chain reaction to amplify segments of the mammaglobin gene from a patient sample. Analysis of the resulting PCR products indicate whether a particular segment of the mammaglobin gene is deleted or rearranged. Such information is useful for prognosis and patient management.

The present invention further provides for methods to detect the presence of the polypeptide, mammaglobin, in a sample obtained from a patient. Any method known in the art for detecting proteins can be used. Such methods include, but are not limited to immunodiffusion, immunoelectrophoresis, immunochemical methods, binder-ligand assays, immunohistochemical techniques, agglutination and complement assays. (for example see *Basic and Clinical Immunology,* Sites and Terr, eds., Appleton & Lange, Norwalk, Conn. pp 217–262, 1991 which is incorporated by reference). Preferred are binder-ligand immunoassay methods including reacting antibodies with an epitope or epitopes of mammaglobin and competitively displacing a labeled mammaglobin protein or derivative thereof.

As used herein, a derivative of mammaglobin is intended to refer to a polypeptide containing amino acids or modified amino acids in which the polypeptide derivative cross-reacts with mammaglobin. By cross-reaction it is meant that an antibody reacts with an antigen other than the one that induced its formation.

Numerous competitive and non-competitive protein binding immunoassays are well known in the art. Antibodies employed in such assays may be unlabeled, for example as used in agglutination tests, or labeled for use a wide variety of assay methods. Labels that can be used include radionuclides, enzymes, fluorescers, chemiluminescers, enzyme substrates or co-factors, enzyme inhibitors, particles, dyes and the like for use in radioimmunoassay (RIA), enzyme immunoassays, e.g., enzyme-linked immunosorbent assay (ELISA), fluorescent immunoassays and the like.

Polyclonal or monoclonal antibodies to mammaglobin or an epitope thereof can be made for use in immunoassays by any of a number of methods known in the art. By epitope reference is made to an antigenic determinant of a polypeptide. An epitope could comprise 3 amino acids in a spacial conformation which is unique to the epitope. Generally an epitope conists of at least 5 such amino acids. Methods of determining the spatial conformation of amino acids are known in the art, and include, for example, x-ray crystallography and 2 dimensional nuclear magnetic resonance.

One approach for preparing antibodies to a protein is the selection and preparation of an amino acid sequence of all or part of the protein, chemically synthesizing the sequence and injecting it into an appropriate animal, usually a rabbit or a mouse.

Methods for preparation of mammaglobin or an epitope thereof include, but are not limited to chemical synthesis, recombinant DNA techniques or isolation from biological samples. Chemical synthesis of a peptide can be performed, for example, by the classical Merrifeld method of solid phase peptide synthesis (Merrifeld, *J Am Chem Soc* 85: 2149, 1963 which is incorporated by reference) or the FMOC strategy on a Rapid Automated Multiple Peptide Synthesis system (DuPont Company, Wilmington, Del.) (Caprino and Han, *J Org Chem* 37: 3404, 1972 which is incorporated by reference).

Polyclonal antibodies can be prepared by immunizing rabbits by injecting antigen into the popliteal lymph nodes followed by subsequent boosts at two week intervals with intraperitoneal injection of antigen. The animals are bled and sera assayed against purified mammaglobin protein usually by ELISA. Monoclonal antibodies can be prepared after the method of Milstein and Kohler by fusing splenocytes from immunized mice with continuously replicating tumor cells such as myeloma or lymphoma cells. (Milstein and Kohler *Nature* 256: 495–497, 1975; Gulfre and Milstein, *Methods in Enzymology: Immunochemical Techniques* 73: 1–46, Langone and Banatis eds., Academic Press, 1981 which are incorporated by reference). The hybridoma cells so formed are then cloned by limiting dilution methods and supernates assayed for antibody production by ELISA or RIA.

The unique ability of antibodies to recognize and specifically bind to target antigens expressed by a tumor cell provides an approach for the treatment of cancer. (For review see LoBuglio and Saleh, *Am J Med Sci* 304: 214–224, 1992; Bagshawe, *Adv Pharmacol* 24: 99–121, 1993 which are incorporated by reference). Thus, another aspect of the present invention provides for a method for preventing the onset and treating breast cancer in an animal based upon the use of antibodies to mammaglobin, which has been discovered to be overexpressed by breast cancer cells. Specific antibodies to mammaglobin, either polyclonal or monoclonal, are produced by any method known in the art. For example, murine or human monoclonal antibodies can be produced by hybridoma technology. Alternatively, mammaglobin, or an immunologically active fragment thereof, or an anti-idiotypic antibody, or fragment thereof can be administered to an animal to elicit the production of antibodies capable of recognizing the mammaglobin-expressing cells.

The antibodies so produced or fragments thereof are labeled with one or more oncolytic substances such as radionuclides, toxins, or cytotoxic drugs and administered to a patient suspected of having breast cancer. The binding of the labeled antibody to the mammaglobin being overexpressed by the breast cancer cell will cause the death of the cancer cell.

Any of a variety of oncolytic substances known in the art can be used to produce such labeled antibodies. For example, immunotoxins can be made by coupling plant and bacterial toxins to antibodies. Such toxins include, for example, ricin, diphtheria toxin and Pseudomonas exotoxin A. Drug-antibody conjugates can also be made in which chemotherapeutic agents are linked to the antibody. Chemotherapeutic agents suitable for such use include, for example, tomoxifen, doxorubicin, methotrexate, chlorambucil, Vinca alkaloids, and mitomycin. In addition, radioimmunoconjugates can be made in which a radionuclide is stably linked to the antibody. Radionuclides suitable for making radioimmunoconjugates include, for example, β-emmitters such as $^{131}I$, $^{188}Re$, $^{186}Re$, $^{67}Cu$, $^{90}Y$ and $^{47}Sc$; α-emitters such as $^{211}At$, $^{212}Bi$ and $^{212}Pb$; auger electron emitters such as $^{125}I$ and $^{77}Br$; and fissionable nuclides such as $^{10}B$.

Preferred embodiments of the invention are described in the following examples. Other embodiments within the scope of the claims herein will be apparent to one skilled in the art from consideration of the specification or practice of the invention as disclosed herein. It is intended that the specification, together with the examples, be considered exemplary only, with the scope and spirit of the invention being indicated by the claims which follow the examples.

In the examples below, cell lines were obtained from American Type Culture Collection and grown in Dulbecco's minimal essential medium supplemented with 10% fetal calf serum. Tissue biopsy specimens were obtained from the Human Cooperative Tissue Network (LiVolsi et al, *Cancer* 71: 1391–1394, 1993 which is incorporated by reference).

EXAMPLE 1

This example illustrates the isolation of mammaglobin cDNA.

Total cellular RNA from the cell line MDA-MB415 was isolated using the standard guanidinium isothiocyanate method. (Belyavsky et al, supra). This RNA was used in the RACE PCR procedure employing the Amplifinder kit (Clonetech) and following the manufacturer's protocol.

The synthesis of first strand cDNA was performed in a standard reaction containing 1 μg RNA, 10 μM specific mammaglobin primer D2R (5'-ATA AGA AAG AGA AGG TGT GG-3')(SEQ ID NO: 4), 4 μl of 5× RT buffer (250 mM TrisCl pH8.3, 375 mM Kcl, 15 mM $MgCl_2$), 2 μl of 100 mM DTT, 1 μl of 10 mM dNTPs and 200 units of Superscript™ II reverse transcriptase (Gibco/BRL) in a reaction volume 20 μl. The reaction proceeded for 1 hour at 45° C. and was terminated by incubating at 95° C. for 5 minutes. RNA was hydrolyzed with 400 μM NaOH at 65° C. for 30 minutes and neutralized with 400 μM acetic acid. Reaction was then added to 3 volumes of 6M NaI and 10 μl of treated glass beads. Beads were washed three times with 80% EtOH and nucleic acid was eluted from the beads in 45 μl of water. Nucleic acid was then precipitated and resuspended in 10 μl of water. The purifed first strand cDNA was ligated to the manufacturer's provided anchor oligonucleotide (SEQ ID NO: 9, 5'-CAC GAA TTC ACT ATC GAT TCT GGA ACC TTC AGA GG-3'), using T4 RNA ligase at 27° for 20 hours. One tenth of a ligation reaction was used for PCR amplification in a 50 μl reaction containing 1 μM manufacturer's anchor primer (SEQ ID NO: 10, 5'-CTG GTT CGG CCC ACC TCT GAA GGT TCC AGA ATC GAT AG-3'), 1 μM mammaglobin specific primer D2Rb (SEQ ID NO: 11, 5'-AAT CCG TAG TTG GTT TCT CAC C-3'), 200 μM dNTPs, 5 units of Vent™ DNA polymerase, and 1× polymerase buffer (10 mM Kcl, 20 mM TrisCl, 10 mM $(NH_4)_2SO_4$, 2 mM $MgSO_4$, 0.1% Triton X-100). The reaction was incubated at 94° for 2 minutes and then 94° for 45 seconds, 50° for 1 minute, and 72° for 90 seconds for a total of 40 times.

The two downstream mammaglobin-specific nested oligonucleotides were D2R (SEQ ID NO: 4) and D2Rb (SEQ ID NO: 11). An upstream mammaglobin-specific control oligonucleotide was also used as per the manufacturer's recommendations, D2F (5'-CTT TCT GCA AGA CCT TTG GC-3') (SEQ ID NO: 12). All PCR amplifications were performed with Vent DNA polymerase (New England Biolabs). The amplified RACE product was digested with EcoRI and ligated into the EcoRI and SmaI sites of the plasmid vector pGEM7Z (Promega).

All sequencing was performed using the Taq DNA polymerase thermal cycle sequencing kit as per the manufacture's protocol (Promega). Briefly the procedure used is as follows.

10 pmol of sequence specific oligonucleotide was end labeled with 10 pmol of $^{32}P$-γ ATP (3,000 Ci/mmol and 10 mCi/ml) using T4 polynucleotide kinase in a 10 μl reaction for 30 minutes at 37° C. A polymerization reaction containing 100 ng of plasmid template, 1.5 pmol of labeled sequencing primer, and 5 units of sequencing grade Taq polymerase was created in 17 μl of the manufacturer's provided sequencing buffer. This reaction was aliquoted to a set of four reaction tubes containing manufacturer's provided mix of deoxynucleotides and either dideoxy-A, C, G, or T. The set of four tubes were incubated at 95° C. for 2 minutes and then, 94° C. for 45 seconds, 45° C. for 30 seconds, and 72° C. for 1 minute for 30 times. After reactions were completed, 3 μl of 80% formamide/bromphenol blue dye was added to each tube. Samples were heated to 70° C. for 2 minutes and loaded on a 6% acrylamide/7.5M urea sequencing gel and run for 2–4 hours and 60 W constant power. The gel was dried and then exposed to Kodak XAR5 Xray film for 2 to 24 hours.

The sequence thus obtained was a 403 bp fragment (SEQ ID NO: 5) as shown in FIG. 2, solid bar. In earlier work the DEST002 Tag sequence was isolated (Watson and Fleming, supra). This sequence was a 206 bp fragment (SEQ ID NO: 6) as shown in FIG. 2, open bar. Combining the information from these two sequences allowed the full-length 503 bp cDNA of mammaglobin to be deduced. (FIG. 2).

EXAMPLE 2

This example demonstrates that mammaglobin expression is restricted to mammary gland tumor cells and to a lesser extent normal mammary gland cells.

Total cellular RNA samples were isolated using the standard guanidinium isothiocyanate method and treated with RNase-free DNase (Promega). For RT/PCR analysis, 1 μg of indicated total RNA was reverse transcribed with oligo $dT_{21}$ (SEQ ID NO:13) and Superscript II reverse transcriptase (Gibco/BRL) according to the manufacture's protocol.

Two hundred ng of oligo $dT_{21}$ (SEQ ID NO: 13) and 1 μg of total RNA were incubated at 65° C. for 5 minutes in a 10 μl volume. Sample was chilled on ice and added to it were 4 μl of 5× RT buffer (250 mM TrisCl pH8.3, 375 mM Kcl, 15 mM $MgCl_2$), 2 μl of 100 mM DTT, 1 μl of 10 mM dNTPs and 200 units of Superscript™ II reverse transcriptase (Gibco/BRL). The reaction proceeded for 1 hour at 45° C. and was terminated by incubating at 95° C. for 5 minutes.

One tenth of each RT reaction was subject to PCR analysis using the mammaglobin specific primers D2R (5'-ATA AGA AAG AGA AGG TGT GG-3') (SEQ ID NO: 4) and d2102 (5'-CAG CGG CTT CCT TGA TCC TTG-3') (SEQ ID NO:3) and standard reaction conditions for 40 cycles at 94°×30 sec./55°×1 min./72°×1 min.

For Northern analysis, 20 μg of total RNA was analyzed as previously described (Watson and Fleming, supra) using the full length mammaglobin cDNA probe. Integrity and equal loading of each RNA sample was assessed by ethidium bromide staining.

As shown in FIG. 4A, the 500 bp mammaglobin message is easily detected in tumor specimen 2410 (the tissue from which this original DEST was isolated) and to a much less extent in normal human breast tissue but not in the immortalized breast epithelial cell line B5-589, or in human lung, placenta, uterus and ovary (FIG. 4A). Following amplification using RT/PCR analysis, mammaglobin expression was still not detected in 15 tissues surveyed (FIG. 4B). Detection of glyceraldehyde 3-phosphate dehydrogenase (GAPDH) message (FIG. 4B) and EGF receptor message (data not shown) in these reactions demonstrated that absence of expression was not due to degraded RNA or other trivial explanations. Thus the expression of mammaglobin mRNA is relatively specific for mammary tissue.

EXAMPLE 3

This example demonstrates that the mammaglobin cDNA encodes a translatable nucleotide sequence which results in protein product of appropriately predicted molecular mass. In vitro translations were performed using the TNT™ rabbit reticulocyte translation kit with T7 RNA polymerase (Promega) and $^{35}$S-Methionine (>1000 Ci/mmol; 10 mCi/ml, Amersham) according to the manufacturer's protocol.

To 25 μl of TNT™ rabbit reticulocyte lystae was added 2 μl of manufacturer's prepared reaction buffer, T7 RNA polymerase, 20 μM amino acid mixture minus methionine, 40 μCi$^{35}$S-methionine (1,000 Ci/mmol and 10 mCi/ml), 40 units ribonuclease inhibitor, 1 μg of mammaglobin/pGEM7 plasmid, and sufficient DEPC treated water to create a final reaction volume of 50 μl. This reaction was incubated at 30° C. for 60 minutes. 5 μl of this reaction was removed into 20 μl of SDS gel buffer, boiled for 2 minutes, and loaded on a 17.5% SDS-polyacrylamide gel.

Rabbit reticulocyte lysate programmed with mammaglobin cDNA produced a 6 kD protein while that programmed with no cDNA did not produce any protein product.

EXAMPLE 4

This example illustrates the prevalence of overexpression of mammaglobin in primary breast carcinoma.

To determine the frequency of mammaglobin overexpression in breast carcinomas, we examined a panel of fifteen, stage I primary breast carcinomas of differing histological types using Northern blot hybridization with the mammaglobin cDNA probe. Patient-matched normal breast tissues samples were also compared in tissues from two patients (FIG. 6). The 500 bp mammaglobin mRNA was detected in normal breast tissue and tumor 2410 and in three other tumors, two of which when tested demonstrated little or no expression in patient-matched normal tissue (BO15 v. BO16; BO22 v. BO23) (FIG. 6). In all, 4 of 15 (27%) of tumors examined overexpressed mammaglobin mRNA. These data indicate that overexpression of mammaglobin is not unique to a single tumor specimen and is, in fact, relatively frequent among primary breast tumors. Furthermore, the fact that all tumors examined were stage I suggests that this dysregulation occurs relatively early in the progression of breast neoplasia.

In view of the above, it will be seen that the several advantages of the invention are achieved and other advantageous results attained.

As various changes could be made in the above methods and compositions without departing from the scope of the invention, it is intended that all matter contained in the above description and shown in the accompanying drawings shall be interpreted as illustrative and not in a limiting sense.

---

What is claimed is:

1. An isolated and purified polypeptide comprising an epitope of mammaglobin, wherein said epitope comprises at least five contiguous amino acids of SEQ ID NO: 2.

2. The polypeptide of claim 1 which comprises SEQ ID NO: 2.

3. The polypeptide of claim 1 which comprises a sequence of 93 amino acids, said sequence being a conservatively substituted derivative of SEQ ID NO: 2, wherein said polypeptide is antigenic.

4. An isolated and purified antibody which is specific for an epitope of mammaglobin comprising at least five contiguous amino acids of SEQ ID NO: 2.

5. The antibody of claim 4 which is generated against a polypeptide comprising SEQ ID NO: 2.

6. The antibody of claim 4 which is generated against a polypeptide comprising a sequence of 93 amino acids, said sequence being a conservatively substituted derivative of SEQ ID NO: 2.

7. The antibody of claim 4, wherein said epitope is secreted by a breast cancer neoplasia cell.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 503 base pairs
        ( B ) TYPE: nucleic acid
        ( C ) STRANDEDNESS: single
        ( D ) TOPOLOGY: linear     ( i i ) MOLECULE TYPE: cDNA to mRNA     ( i i i ) HYPOTHETICAL: NO     ( i v ) ANTI-SENSE: NO     ( x i ) SEQUENCE DESCRIPTION: SEQ ID NO:1:

```
GACAGCGGCT    TCCTTGATCC    TTGCCACCCG    CGACTGAACA    CCGACAGCAG    CAGCCTCACC         60

ATGAAGTTGC    TGATGGTCCT    CATGCTGGCG    GCCCTCTCCC    AGCACTGCTA    CGCAGGCTCT        120

GGCTGCCCCT    TATTGGAGAA    TGTGATTTCC    AAGACAATCA    ATCCACAAGT    GTCTAAGACT        180

GAATACAAAG    AACTTCTTCA    AGAGTTCATA    GACGACAATG    CCACTACAAA    TGCCATAGAT        240

GAATTGAAGG    AATGTTTTCT    TAACCAAACG    GATGAAACTC    TGAGCAATGT    TGAGGTGTTT        300
```

```
ATGCAATTAA  TATATGACAG  CAGTCTTTGT  GATTTATTTT  AACTTTCTGC  AAGACCTTTG      360

GCTCACAGAA  CTGCAGGGTA  TGGTGAGAAA  CCAACTACGG  ATTGCTGCAA  ACCACACCTT      420

CTCTTTCTTA  TGTCTTTTTA  CTACAAACTA  CAAGACAATT  GTTGAAACCT  GCTATACATG      480

TTTATTTTAA  TAAATTGATG  GCA                                                 503
```

(2) INFORMATION FOR SEQ ID NO:2:

(i) SEQUENCE CHARACTERISTICS:
        (A) LENGTH: 93 amino acids
        (B) TYPE: amino acid
        (C) STRANDEDNESS: single
        (D) TOPOLOGY: linear     (ii) MOLECULE TYPE: protein     (iii) HYPOTHETICAL: NO     (xi) SEQUENCE DESCRIPTION: SEQ ID NO:2:

```
Met  Lys  Leu  Leu  Met  Val  Leu  Met  Leu  Ala  Ala  Leu  Ser  Gln  His  Cys
 1              5                        10                       15
Tyr  Ala  Gly  Ser  Gly  Cys  Pro  Leu  Leu  Glu  Asn  Val  Ile  Ser  Lys  Thr
              20                       25                       30
Ile  Asn  Pro  Gln  Val  Ser  Lys  Thr  Glu  Tyr  Lys  Glu  Leu  Leu  Gln  Glu
              35                       40                       45
Phe  Ile  Asp  Asp  Asn  Ala  Thr  Thr  Asn  Ala  Ile  Asp  Glu  Leu  Lys  Glu
         50                       55                       60
Cys  Phe  Leu  Asn  Gln  Thr  Asp  Glu  Thr  Leu  Ser  Asn  Val  Glu  Val  Phe
 65                       70                       75                       80
Met  Gln  Leu  Ile  Tyr  Asp  Ser  Ser  Leu  Cys  Asp  Leu  Phe
                   85                       90
```

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: cDNA     (iii) HYPOTHETICAL: NO     (iv) ANTI-SENSE: NO     (xi) SEQUENCE DESCRIPTION: SEQ ID NO:3:

```
CAGCGGCTTC  CTTGATCCTT  G                                                    21
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: cDNA     (iii) HYPOTHETICAL: NO     (iv) ANTI-SENSE: NO     (xi) SEQUENCE DESCRIPTION: SEQ ID NO:4:

```
ATAAGAAAGA  GAAGGTGTGG                                                       20
```

(2) INFORMATION FOR SEQ ID NO:5:

(i) SEQUENCE CHARACTERISTICS:
    (A) LENGTH: 403 base pairs
    (B) TYPE: nucleic acid
    (C) STRANDEDNESS: single
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:5:

| | | | | | | |
|---|---|---|---|---|---|---|
| GACAGCGGCT | TCCTTGATCC | TTGCCACCCG | CGACTGAACA | CCGACAGCAG | CAGCCTCACC | 60 |
| ATGAAGTTGC | TGATGGTCCT | CATGCTGGCG | GCCCTCTCCC | AGCACTGCTA | CGCAGGCTCT | 120 |
| GGCTGCCCCT | TATTGGAGAA | TGTGATTTCC | AAGACAATCA | ATCCACAAGT | GTCTAAGACT | 180 |
| GAATACAAAG | AACTTCTTCA | AGAGTTCATA | GACGACAATG | CCACTACAAA | TGCCATAGAT | 240 |
| GAATTGAAGG | AATGTTTTCT | TAACCAAACG | GATGAAACTC | TGAGCAATGT | TGAGGTGTTT | 300 |
| ATGCAATTAA | TATATGACAG | CAGTCTTTGT | GATTTATTTT | AACTTTCTGC | AAGACCTTTG | 360 |
| GCTCACAGAA | CTGCAGGGTA | TGGTGAGAAA | CCAACTACGG | ATT | | 403 |

(2) INFORMATION FOR SEQ ID NO:6:

(i) SEQUENCE CHARACTERISTICS:
    (A) LENGTH: 206 base pairs
    (B) TYPE: nucleic acid
    (C) STRANDEDNESS: single
    (D) TOPOLOGY: linear (ii) MOLECULE TYPE: cDNA to mRNA (iii) HYPOTHETICAL: NO (iv) ANTI-SENSE: NO (xi) SEQUENCE DESCRIPTION: SEQ ID NO:6:

| | | | | | | |
|---|---|---|---|---|---|---|
| TTTATGCAAT | TAATATATGA | CAGCAGTCTT | TGTGATTTAT | TTTAACTTTC | TGCAAGACCT | 60 |
| TTGGCTCACA | GAACTGCAGG | GTATGGTGAG | AAACCAACTA | CGGATTGCTG | CAAACCACAC | 120 |
| CTTCTCTTTC | TTATGTCTTT | TTACTACAAA | CTACAAGACA | ATTGTTGAAA | CCTGCTATAC | 180 |
| ATGTTTATTT | TAATAAATTG | ATGGCA | | | | 206 |

(2) INFORMATION FOR SEQ ID NO:7:

(i) SEQUENCE CHARACTERISTICS:
    (A) LENGTH: 95 amino acids
    (B) TYPE: amino acid
    (C) STRANDEDNESS: single
    (D) TOPOLOGY: linear (ii) MOLECULE TYPE: protein (iii) HYPOTHETICAL: NO (xi) SEQUENCE DESCRIPTION: SEQ ID NO:7:

```
Met Lys Leu Val Phe Leu Phe Leu Leu Val Thr Ile Pro Ile Cys Cys
 1               5                  10                  15
Tyr Ala Ser Gly Ser Gly Cys Ser Ile Leu Asp Glu Val Ile Arg Gly
            20                  25                  30
Thr Ile Asn Ser Thr Val Thr Leu His Asp Tyr Met Lys Leu Val Lys
        35                  40                  45
```

```
Pro  Tyr  Val  Gln  Asp  His  Phe  Thr  Glu  Lys  Ala  Val  Lys  Gln  Phe  Lys
          50                       55                  60

Gln  Cys  Phe  Leu  Asp  Gln  Thr  Asp  Lys  Thr  Leu  Glu  Asn  Val  Gly  Val
65                       70                  75                            80

Met  Met  Glu  Ala  Ile  Phe  Asn  Ser  Glu  Ser  Cys  Gln  Gln  Pro  Ser
               85                       90                       95
```

( 2 ) INFORMATION FOR SEQ ID NO:8:

( i ) SEQUENCE CHARACTERISTICS:
        ( A ) LENGTH: 91 amino acids
        ( B ) TYPE: amino acid
        ( C ) STRANDEDNESS: single
        ( D ) TOPOLOGY: linear     ( i i ) MOLECULE TYPE: protein     ( i i i ) HYPOTHETICAL: NO     ( x i ) SEQUENCE DESCRIPTION: SEQ ID NO:8:

```
Met  Lys  Leu  Ala  Val  Thr  Leu  Thr  Leu  Val  Thr  Leu  Ala  Leu  Cys  Cys
1                   5                        10                       15

Ser  Ser  Ala  Ser  Ala  Glu  Ile  Cys  Pro  Ser  Phe  Gln  Arg  Val  Ile  Glu
               20                  25                            30

Thr  Leu  Leu  Met  Asp  Thr  Pro  Ser  Ser  Tyr  Glu  Ala  Ala  Met  Glu  Leu
          35                       40                       45

Phe  Ser  Pro  Asp  Gln  Asp  Met  Arg  Glu  Ala  Gly  Ala  Gln  Leu  Lys  Lys
     50                       55                       60

Leu  Val  Asp  Thr  Leu  Pro  Gln  Lys  Pro  Arg  Glu  Ser  Ile  Ile  Lys  Leu
65                       70                  75                            80

Met  Glu  Lys  Ile  Ala  Gln  Ser  Ser  Leu  Cys  Asn
               85                       90
```

( 2 ) INFORMATION FOR SEQ ID NO:9:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: NO     ( x i ) SEQUENCE DESCRIPTION: SEQ ID NO:9:

```
CACGAATTCA  CTATCGATTC  TGGAACCTTC  AGAGG                                    35
```

( 2 ) INFORMATION FOR SEQ ID NO:10:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: NO     ( x i ) SEQUENCE DESCRIPTION: SEQ ID NO:10:

```
CTGGTTCGGC  CCACCTCTGA  AGGTTCCAGA  ATCGATAG                                 38
```

(2) INFORMATION FOR SEQ ID NO:11:

(i) SEQUENCE CHARACTERISTICS:
        (A) LENGTH: 22 base pairs
        (B) TYPE: nucleic acid
        (C) STRANDEDNESS: single
        (D) TOPOLOGY: linear     (ii) MOLECULE TYPE: cDNA     (iii) HYPOTHETICAL: NO     (iv) ANTI-SENSE: NO     (xi) SEQUENCE DESCRIPTION: SEQ ID NO:11:

AATCCGTAGT TGGTTTCTCA CC     22

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: cDNA     (iii) HYPOTHETICAL: NO     (iv) ANTI-SENSE: NO     (xi) SEQUENCE DESCRIPTION: SEQ ID NO:12:

CTTTCTGCAA GACCTTTGGC     20

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: cDNA to mRNA     (iii) HYPOTHETICAL: NO     (iv) ANTI-SENSE: NO     (xi) SEQUENCE DESCRIPTION: SEQ ID NO:13:

TTTTTTTTT TTTTTTTTT T     21